(12) United States Patent
Garavaglia et al.

(10) Patent No.: US 11,587,648 B1
(45) Date of Patent: Feb. 21, 2023

(54) SYSTEMS AND METHODS FOR ANALYZING CAPTURED BIOMETRIC DATA

(71) Applicant: State Farm Mutual Automobile Insurance Company, Bloomington, IL (US)

(72) Inventors: Jeremy Garavaglia, Mesa, AZ (US); John Larson, Normal, IL (US); Jovonni Lee Pharr, Mableton, GA (US); Kip Wilson, Cave Creek, AZ (US); Nolan White, Chandler, AZ (US); Achyutha Srinivas Mudunuri, Gilbert, AZ (US); Wallace Taylor, Tempe, AZ (US); Mike Aviles, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 39 days.

(21) Appl. No.: 16/950,590

(22) Filed: Nov. 17, 2020

Related U.S. Application Data

(63) Continuation of application No. 15/697,095, filed on Sep. 6, 2017, now Pat. No. 10,878,062.

(51) Int. Cl.
*G06Q 40/08* (2012.01)
*G16H 10/40* (2018.01)
(Continued)

(52) U.S. Cl.
CPC ............ *G16H 10/40* (2018.01); *G06Q 40/08* (2013.01); *G06V 40/70* (2022.01); *G16H 40/60* (2018.01)

(58) Field of Classification Search
CPC ....................................... G06Q 40/08
(Continued)

(56) References Cited

U.S. PATENT DOCUMENTS

| 8,224,677 | B2 | 7/2012 | Reynolds et al. |
| 8,510,133 | B2 | 8/2013 | Peak et al. |

(Continued)

OTHER PUBLICATIONS

Tedesco et al., "A Review of Activity Trackers for Senior Citizens: Research Perspectives, Commercial Landscape and the Role of the Insurance Industry", Published Online: Jun. 3, 2017, 39 pages, retrieved from URL: https://www.ncbi.nlm.nih.gov/pmc/articles/PMC5492436/.

*Primary Examiner* — William E Rankins
(74) *Attorney, Agent, or Firm* — Armstrong Teasdale LLP

(57) ABSTRACT

A computer system for analyzing biometric data of a user collected from a plurality of user devices and used to generate an insurance policy for the user includes a processor and a non-transitory, tangible, computer-readable storage medium having instructions stored thereon that, in response to execution by the processor, cause the processor to perform operations including: (i) receiving, from a wearable electronic user device, biometric data associated with a user; (ii) analyzing, based upon a plurality of rules, the biometric data; (iii) determining a health score associated with the user, based in part upon the analysis of the biometric data, wherein the health score represents a likelihood that the user will maintain a level of health for a predefined period of time; (iv) retrieving terms and conditions for an insurance policy from a database based upon the health score; and (v) generating, based upon the determining, an insurance policy for the user based upon the terms and conditions.

21 Claims, 7 Drawing Sheets

(51) Int. Cl.
*G06V 40/70* (2022.01)
*G16H 40/60* (2018.01)

(58) Field of Classification Search
USPC .............................................................. 705/4
See application file for complete search history.

(56) References Cited

U.S. PATENT DOCUMENTS

| | | |
|---|---|---|
| 8,660,865 B2 | 2/2014 | Reynolds et al. |
| 9,224,171 B2 | 12/2015 | Peak et al. |
| 9,558,520 B2 | 1/2017 | Peak et al. |
| 9,721,066 B1 | 8/2017 | Funaro et al. |
| 10,430,887 B1 * | 10/2019 | Parker .................... G06Q 40/08 |
| 10,629,293 B2 | 4/2020 | Jiao et al. |
| 2002/0156654 A1 | 10/2002 | Roe et al. |
| 2006/0218023 A1 * | 9/2006 | Conrad .................. G16H 20/10 |
| | | 705/3 |
| 2007/0047770 A1 | 3/2007 | Swope et al. |
| 2011/0004492 A1 | 1/2011 | Bradshaw et al. |
| 2013/0035945 A1 | 2/2013 | Seville |
| 2015/0025917 A1 | 1/2015 | Stempora |
| 2016/0247017 A1 | 8/2016 | Sareen et al. |
| 2016/0361027 A1 | 12/2016 | Jang et al. |
| 2017/0046652 A1 | 2/2017 | Haldenby et al. |
| 2017/0147775 A1 | 5/2017 | Ohnemus et al. |
| 2019/0096000 A1 | 3/2019 | Boesen |

\* cited by examiner

Flexible Schema

| UID | STRING |
|-----|--------|
| UID1 | {"hr":"75", "steps":"8000"} |
| UID1 | {"hr":"80", "steps":"9000"} |
| UID1 | {"hr":"65", "steps":"7500"} |

FIG. 4

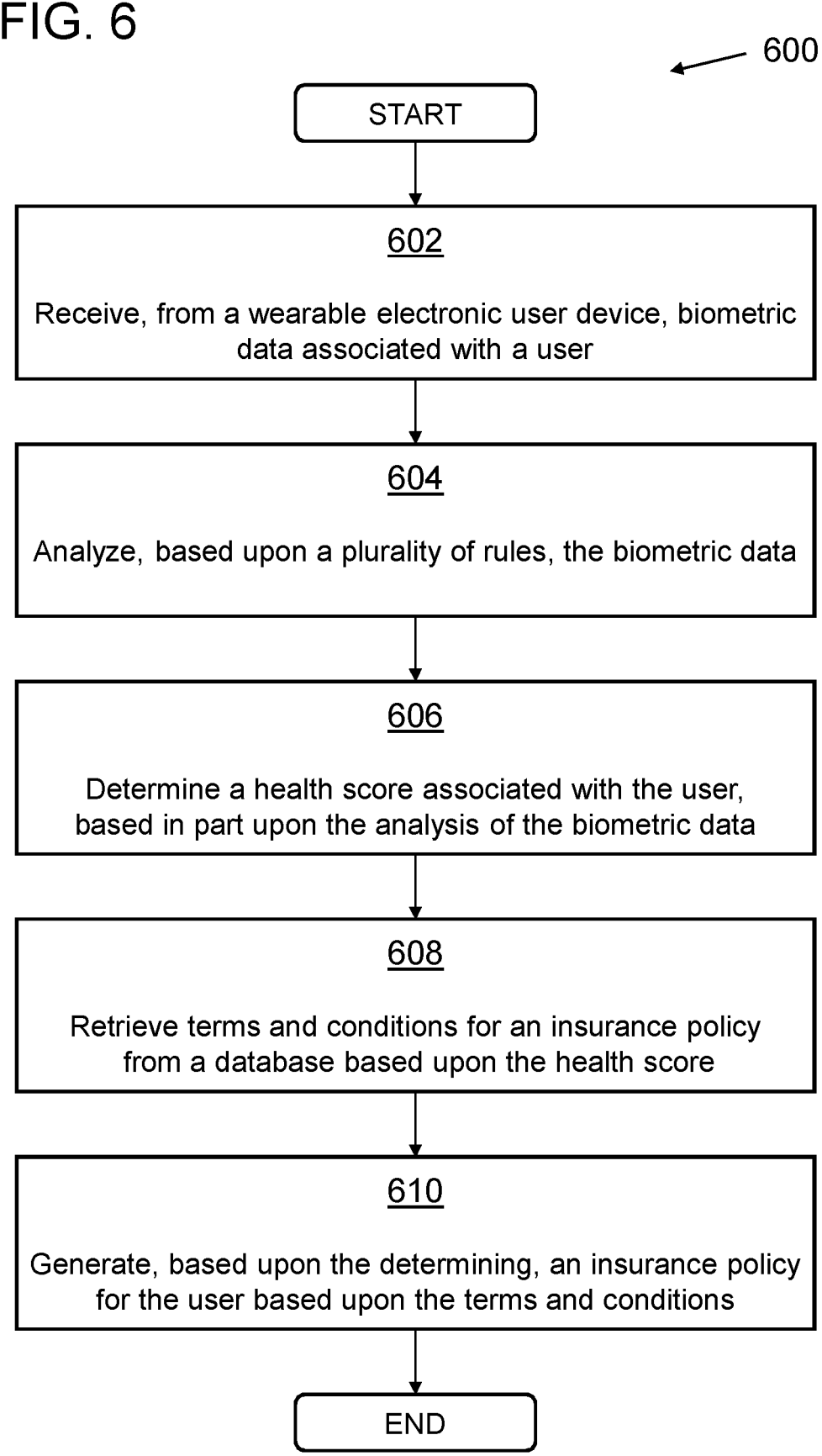

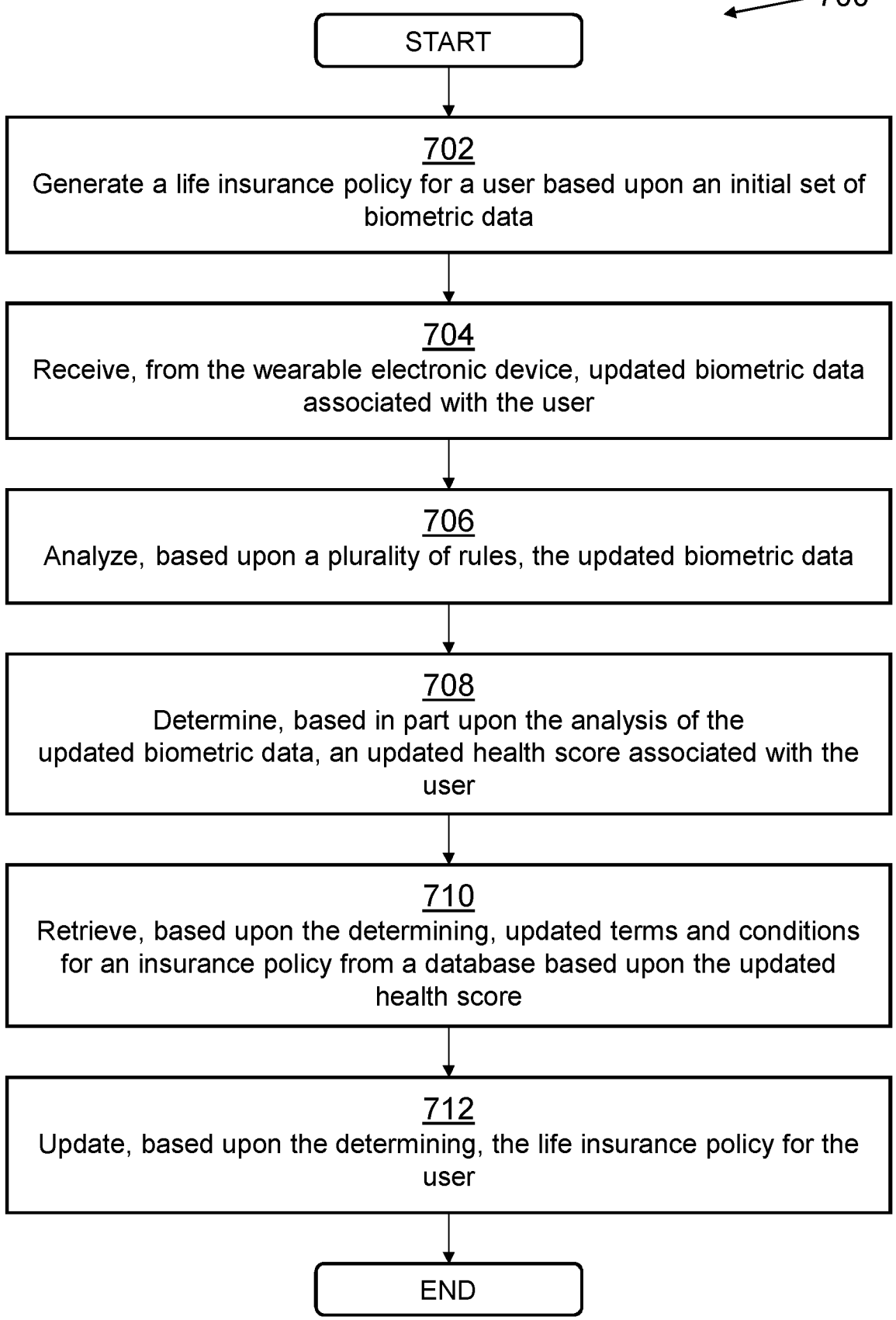

SYSTEMS AND METHODS FOR ANALYZING CAPTURED BIOMETRIC DATA

CROSS-REFERENCE TO RELATED APPLICATIONS

This application is a continuation of and claims priority to U.S. patent application Ser. No. 15/697,095, filed Sep. 6, 2017, all of which is incorporated herein by reference in its entirety.

FIELD OF THE INVENTION

The present disclosure relates to systems and methods for analyzing biometric data that is captured by a variety of devices and, more particularly, to network-based systems and methods for analyzing biometric data to assess a person's mortality risk, wherein the biometric data is captured by a variety of devices including wearable electronic devices, home based devices, vehicle based devices, and other client devices.

BACKGROUND

Biometric data is currently captured by a large variety of devices, such as, for example, wearable electronic devices (e.g., fitness bands), smartphones, various home based devices (e.g., smart refrigerators and smart scales), and vehicle based devices. However, at present, such data is not typically collected at a central location, such as a central database server, for evaluation and analysis.

In addition, in the insurance industry, it is common to assess a user's mortality risk for the purpose of providing an insurance policy (e.g., a health insurance policy) to the user. Typically, such insurance policies are provided based upon the results of one or more medical examinations, such as, for example, data obtained from various physical examinations, blood tests, and the like. This data, which may be referred to as "medical data," may be evaluated, and a risk, such as a mortality risk, associated with a user being examined may be determined.

The mortality risk may, in turn, be used to underwrite an insurance policy, such as, for example, a life insurance policy. Specifically, a mortality risk may affect a life insurance premium. For instance, as a user's risk of mortality increases, the dollar amount associated with the premium may increase, and as the user's risk of mortality decreases, the dollar amount associated with the premium may decrease.

However, many such systems may only collect medical data at a single point in time, such as at the time the policy is established. In addition, many conventional life insurance policies may be underwritten for a long term, such as, for example, for a term of ten, twenty, or even thirty years. During this time, a premium may not be updated or revised based upon changes in the user's mortality risk. For example, although a user's medical examinations may indicate that the user is in good health at the inception of the policy, over time, the user may develop certain unhealthy habits, which may contribute to a deterioration or reduction in the overall health of the user.

Thus, many conventional life insurance policies are not based upon the wealth of biometric data available from the large number of electronic devices currently collecting such data. In addition, many conventional life insurance policies may require that a user undergo one or more potentially unpleasant medical examinations. Further still, many conventional life insurance policies are not updated based upon the user's lifestyle and/or variations in the user's overall health.

BRIEF SUMMARY

The present embodiments may relate to systems and methods for analyzing captured biometric data. In one aspect, a computer system for analyzing biometric data of a user collected from a plurality of user devices and used to generate an insurance policy for the user is provided. In some exemplary embodiments, the computer system includes a processor and a non-transitory, tangible, computer-readable storage medium having instructions stored thereon that, in response to execution by the processor, cause the processor to perform operations including: (i) receiving, from a wearable electronic user device, biometric data associated with a user; (ii) analyzing, based upon a plurality of rules, the biometric data; (iii) determining a health score associated with the user, based in part upon the analysis of the biometric data, wherein the health score represents a likelihood that the user will maintain a level of health for a predefined period of time; (iv) retrieving terms and conditions for an insurance policy from a database based upon the health score; and (v) generating, based upon the determining, an insurance policy for the user based upon the terms and conditions.

In another aspect, at least one tangible, non-transitory, computer readable storage media having computer-executable instructions embodied thereon, wherein when executed by at least one processor, the computer-executable instructions cause the processor to: (i) receive, from a wearable electronic user device, biometric data associated with a user; (ii) analyze, based upon a plurality of rules, the biometric data; (iii) determine a health score associated with the user, based in part upon the analysis of the biometric data, wherein the health score represents a likelihood that the user will maintain a level of health for a predefined period of time; (iv) retrieve terms and conditions for an insurance policy from a database based upon the health score; and (v) generate, based upon the determining, an insurance policy for the user based upon the terms and conditions.

In yet another aspect, a method computer system for analyzing biometric data of a user collected from a plurality of user devices and used to generate an insurance policy for the user is provided. The method includes (i) receiving, from a wearable electronic user device, biometric data associated with a user; (ii) analyzing, based upon a plurality of rules, the biometric data; (iii) determining a health score associated with the user, based in part upon the analysis of the biometric data, wherein the health score represents a likelihood that the user will maintain a level of health for a predefined period of time; (iv) retrieving terms and conditions for an insurance policy from a database based upon the health score; and (v) generating, based upon the determining, an insurance policy for the user based upon the terms and conditions.

In yet another aspect, a computer system for analyzing biometric data of a user collected from a plurality of user devices and used to generate an insurance policy for the user is provided. In some exemplary embodiments, the computer system includes a processor and a non-transitory, tangible, computer-readable storage medium having instructions stored thereon that, in response to execution by the processor, cause the processor to perform operations including: (i) generating a life insurance policy for a user based upon an initial set of biometric data; (ii) receiving, from the wearable electronic device, updated biometric data associated with the user; (iii) analyzing, based upon a plurality of rules, the updated biometric data; (iv) determining, based in part upon the analysis of the updated biometric data, an updated health score associated with the user, wherein the updated health score represents an updated likelihood that the user will maintain a level of health for a predefined period of time; (v) retrieving, based upon the determining, updated terms and conditions for an insurance policy from a database based upon the updated health score; and (vi) updating, based upon the determining, the life insurance policy for the user.

Advantages will become more apparent to those skilled in the art from the following description of the preferred embodiments which have been shown and described by way of illustration. As will be realized, the present embodiments may be capable of other and different embodiments, and their details are capable of modification in various respects. For example, and as described herein, the data capture and analysis processes described herein may include functionality that permits a user to "opt in" and/or "opt out" of these processes, such that the user's privacy is preserved. Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein:

FIG. 4 illustrates a data table for use with the system shown in FIG. 1;

FIG. 6 illustrates a flow chart of an exemplary computer-implemented process for collecting and analyzing biometric data of a user for generating a health score.

FIG. 7 illustrates a flow chart of an exemplary computer-implemented process for updating a health score.

Figure 1:
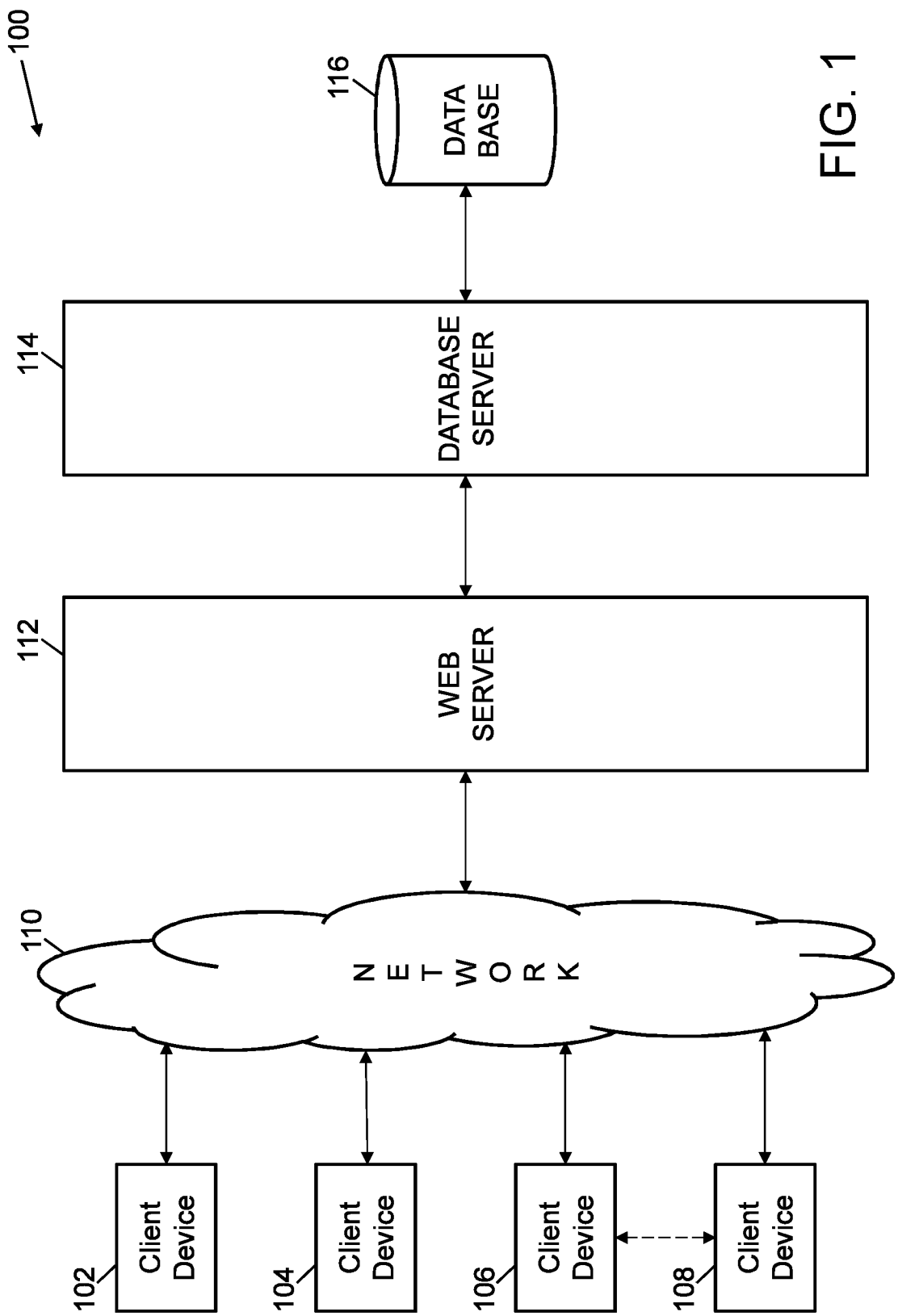
FIG. 1 illustrates a schematic diagram of an exemplary biometric analysis computer system for collecting and analyzing biometric data of a user for generating a health score.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION OF THE DRAWINGS

The present embodiments may relate to, inter alia, systems and methods for collecting and analyzing biometric data of a user for generating a health score. In one exemplary embodiment, the process may be performed by at least one front-end system, such as a client device, and at least one back-end system, such as a web server and/or a database server.

As used herein, the term "biometric data" may refer to the measurement and/or analysis of physical and/or behavioral characteristics, such as, but not limited to: a person's height, weight, age, heart rate, driving habits, eating habits, and the like. As described in greater detail below, biometric data may include, but is not limited to, any data that may be collected by a wearable electronic user device, any data that may be collected by a device within a home of the user (e.g. "home data"), and/or any data that may be collected by a vehicle of a user (e.g., "vehicle data"), Accordingly, the system may include a plurality of client devices that are used for collecting a variety of biometric data, such as a wearable electronic device, a device associated with a home or dwelling (e.g., a "home based device"), a device associated with a vehicle (e.g., a "vehicle based device"), such as an automobile, and a mobile communications device, such as a smartphone. Each client device may be coupled through a network to a web server, which may interface with a database server to read and write data to a database coupled to the database server.

Each client device may collect data, such as, for example, data associated with a user interested in obtaining a life insurance policy. For instance, a wearable electronic device, such as a fitness bracelet, may detect or measure biometric data of the user, such as the user's heart rate, a number of steps taken by the user on a daily basis, the user's sleep patterns, and the like. Similarly, a client device within a user's home, such as a smart refrigerator or an air quality monitoring device, may detect or measure other biometric data associated with the user's home, such as, for example, food items within the user's refrigerator, an air quality within the dwelling, and the like. In addition, a client device associated with a vehicle of the user, such as an accelerometer or GPS system, may collect other biometric data indicative of the user's driving habits, locations to which the user travels, and the like. Moreover, a smartphone may collect a variety of personal data associated with the user, such as, for example, social networking data, user profile data, shopping or purchasing activity data, and the like. As used herein, and for convenience, the biometric and personal data described herein may be referred to as "lifestyle data." In various embodiments the lifestyle data captured and analysis processes described herein may include functionality that permits a user to "opt in" and/or "opt out" of these processes, such that the user's privacy is preserved.

Thus, each client device may collect a variety of biometric and/or personal data associated with the user. This data may be generally representative of the daily activities and/or habits of the user and may be provided to and analyzed by the web server. For example, the web server may analyze one or more of the types of lifestyle data described above to determine a health score associated with the user. In the exemplary embodiment, the health score is a score (which may be associated with a mortality risk) that represents a risk or likelihood that the user will die within a predefined period of time, and which may vary by user based upon the totality of data collected for the user. For example, a user whose biometric and/or personal data suggests good health may be associated with a low mortality risk (e.g., a high health score), while a user whose biometric data suggests poor health may be associated with a higher mortality risk (e.g., a lower health score).

The web server may, in addition, generate a life insurance policy for the user based upon the determined health score. More particularly, the web server may generate a life insurance policy premium, based upon the mortality risk. As the mortality risk increases, the premium may also increase, and as the mortality risk decreases, the premium may also decrease. Thus, a user's life insurance policy premium may be dependent upon (and/or proportional to) the user's health score (or mortality risk), as determined by the system based upon biometric and/or personal associated with the user. Further, in certain embodiments, an existing life insurance policy (and associated premium) may be periodically updated based upon periodically collected biometric and/or personal data, such that a user's premium may fluctuate of a term of the life insurance policy based upon a fluctuating health score and/or mortality risk of the user over time.

Exemplary technical effects of the systems, methods, and computer-readable media described herein may include, for example: (a) generation of a life insurance policy, including a life insurance policy premium, based upon lifestyle data, such as biometric data and/or personal data; and (b) updating of a life insurance policy, including a life insurance policy premium, based upon lifestyle data, such as biometric data and/or personal data.

Exemplary System for Generating a Health Score

FIG. 1 depicts a view of an exemplary system 100 for collecting and analyzing biometric data of a user for generating a health score that can be used to create an insurance policy for the user. In one exemplary embodiment, system 100 may include a plurality of client devices, such as a first client device 102, a second client device 104, a third client device 106, and/or a fourth client device 108. Each client device 102-108 may be associated with an individual, such as a user who has purchased, or who is interested in purchasing, a life insurance policy. In this sense, the user may be referred to herein as an "applicant," such as an applicant for a life insurance policy. System 100 may also include (as described in greater detail below), a network 110, a web server 112, a database server 114, and/or a database 116.

In various embodiments, one or more clients devices, such as first client device 102, second client device 104, third client device 106, and/or fourth client device 108 may be configured to implement the data capture and analysis processes described herein. Client devices 102-108 may, for example, be configured to implement all or a portion of these processes, such that at least a portion of the processing requirements are removed from a backend portion of system 100, such as, for example, from web server 112 and/or database server 114. Thus, in some embodiments, data being processed may be distributed between a plurality of client devices and/or one or more devices on a backend system, such as web server 112 and/or database server 114.

In addition, although a variety of data capture and analysis processes are described in detail below, it will be appreciated that a user may opt into and/or opt out of such data capture and analysis processes, such that the user's privacy is preserved.

Accordingly, in the exemplary, first client device 102 may be a wearable electronic user device configured to detect and/or measure biometric data of the user. For example, first client device 102 may be a fitness bracelet, a smart watch, an electronic scale (e.g., a smart scale), a bed (e.g., an electronic bed), a blood pressure monitor, an electronic dermal patch, and/or any other device configured to be worn by the user and configured, during operation, to track and/or collect biometric data of the user.

As described above, biometric data may refer to any physical and/or behavioral characteristics of a user. Biometric data collected by a wearable user electronic device may include skin temperature data, heart rate data, body mass index data, resting heart rate data, exercise intensity data, calories burned data, sleep data (such as REM sleep duration data) electrocardiogram data, VO2 max data, steps taken data, floors climbed data, blood pressure data, blood oxygen content data, weight data, height data, and the like.

Second client device 104 may be any electronic device associated with the user's home or dwelling that is configured to detect and/or measure biometric data of the user, such as, for example, home data (as described above). In the exemplary embodiment, home data may include, but is not limited to, data such as data collected by a smart refrigerator (e.g., including an amount and types of foods purchased), a thermostat, one or more air quality sensors, and/or any other device configured to operate within the user's home or dwelling.

Thus, as used herein, home data may include any data that may be collected and/or measured in association with a home or dwelling, such as environmental air quality data, home temperature data, ultraviolet radiation exposure data, carbon dioxide data, carbon monoxide data, amounts and types of foods purchased, and the like. In some embodiments, home data may include data associated with other structures, such as office buildings and other structures frequented and/or visited by the user.

Third client device 106 may be any electronic device operating within a vehicle of the user that is configured to detect and/or measure biometric data of the user, such as, for example, vehicle data (as described above). In the exemplary embodiment, a device operating within a vehicle may include, for example, an accelerometer, an odometer, a fuel gauge, a GPS system, a radar system, and the like. In addition, as described herein, vehicle data may include, for example, a driving history or driving behavior of the user, GPS data, location data, speed data, distance data, vehicle safety and/or vehicle operating conditions, and the like.

Fourth client device 108 may be any personal computing device and/or any mobile communications device of the user, such as a personal computer, a tablet computer, a smartphone, and the like. Fourth client device 108 may be configured to detect, collect, or otherwise obtain personal information associated with the user, such as, for example, social networking data associated with the user, one or more user profiles of the user, shopping preferences and/or historical online shopping activities of the user (e.g., online purchases, such as online purchases of food and sundries, such as cigarettes, pharmaceuticals, and the like).

Accordingly, first client device 102, second client device 104, third client device 106, and/or fourth client device 108 may collect a variety of data, such as, for example, biometric data (including home data and vehicle data) and/or personal data. Further, for convenience, these data may be collectively referred to herein as "lifestyle data."

Network 110 may be any electronic communications system, such as any computer network or collection of computer networks, and may incorporate various hardware and/or software. Communication over network 110 may be accomplished via any suitable communication channels, such as, for example, one or more telephone networks, one or more extranets, one or more intranets, the Internet, one or more point of interaction devices (e.g., point of sale devices, smart phones, cellular phones), various online and/or offline communications systems, such as various local area and wide area networks, and the like.

Web server 112 may be any computer or computer system that is configured to receive and process requests made via HTTP. Web server 112 may be coupled between client devices 102-108 and database server 114. More particularly, web server 112 may be communicatively coupled to client devices 102-108 via network 110. In various embodiments, web server 112 may be directly coupled to database server 114 and/or communicatively coupled to database server 114 via a network, such as network 110. Web server 112 may, in addition, function to store, process, and/or deliver one or more web pages and/or any other suitable content to client devices 102-108. In addition, any of client devices 102-108 may include, or implement, an application (or an "app") that interacts with web server 112 and that is configured to store, process, and/or deliver one or more web pages and/or any other suitable content to client devices 102-108. Web server 112 may, in addition, receive data, such as biometric data, home data, vehicle data, and/or personal data (as described herein) from one or more client devices 102-108 for subsequent transmission to database server 114.

In various embodiments, web server 112 may implement various hardware and/or software, such as, for example, one or more communication protocols, one or more message brokers, one or more data processing engines, one or more servlets, one or more application servers, and the like. For instance, in one embodiment, web server 112 may implement an Internet of Things (IoT) protocol, such as a machine-to-machine IoT communications protocol (e.g. an MQTT protocol). In addition, in various embodiments, web server 112 may implement a message broker program module configured to translate a message or communications from a messaging protocol of a sending device to a messaging protocol of a receiving device (e.g., RABBITMQ, KAFKA, ACTIVEMQ, KESTREL). Further still, in some embodiments, web server 112 may implement a data processing engine, such as a cluster computing framework like APACHE SPARK. In addition, in various embodiments, web server 112 may implement servlet and/or JSP server, such as APACHE TOMCAT.

Database server 114 may be any computer or computer program that provides database services to one or more other computers or computer programs. In various embodiments, database server 114 may be communicatively coupled between web server 112 and database 116. Database server 114 may, in addition, function to process data received from web server 112, such as biometric data, home data, vehicle data, and/or personal data (as described herein), for storage within database 116.

Database 116 may be any organized collection of data, such as, for example, any data organized as part of a relational data structure, any data organized as part of a flat file, and the like. Database 116 may be communicatively coupled to database server 114 and may receive data from, and provide data to, database server 114, such as in response to one or more requests for data, which may be provided via a database management system (DBMS) implemented on database server 114. In various embodiments, database 116 may be a non-relational database, such as an APACHE HADOOP database.

Although the components of system 100 are described below and depicted at FIG. 1 as being interconnected in a particular configuration, it is contemplated that the systems, subsystems, hardware and software components, various network components, and database systems described herein may be variously configured and interconnected and may communicate with one another within system 100 to facilitate the processes and advantages described herein. For example, although a single web server 112, a single database server 114, and a single database 116 are described above, it will be appreciated that system 100 may include any suitable number of interconnected, communicatively coupled, web servers, database servers, and/or databases. Further, although certain functions, processes, and operations are described herein with respect to one or more system components, it is contemplated that one or more other system components may perform the functions, processes, and operations described herein.

Exemplary Client Device

Figure 2:
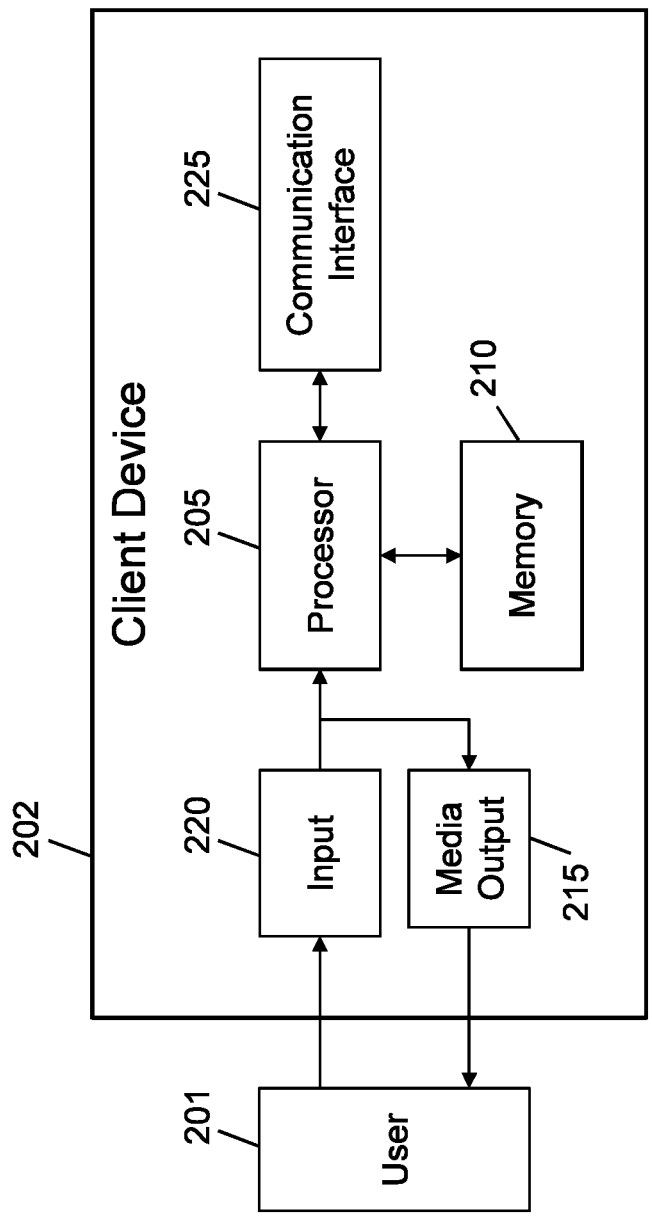
FIG. 2 illustrates an exemplary configuration of a client device shown in FIG. 1, in accordance with one embodiment of the present disclosure.

FIG. 2 depicts an exemplary configuration of a client device 202, such as client devices 102-108, as shown in FIG. 1, and in accordance with one embodiment of the present disclosure. Client device 202 may be operated by a user 201. Client device 202 may include a processor 205 for executing instructions. In some embodiments, executable instructions may be stored in a memory area 210. Processor 205 may include one or more processing units (e.g., in a multi-core configuration). Memory area 210 may be any device allowing information such as executable instructions and/or transaction data to be stored and retrieved. Memory area 210 may include one or more computer readable media.

Client device 202 may also include at least one media output component 215 for presenting information to user 201. Media output component 215 may be any component capable of conveying information to user 201. In some embodiments, media output component 215 may include an output adapter (not shown) such as a video adapter and/or an audio adapter. An output adapter may be operatively coupled to processor 205 and adapted to operatively couple to an output device such as a display device (e.g., a cathode ray tube (CRT), liquid crystal display (LCD), light emitting diode (LED) display, or "electronic ink" display) or an audio output device (e.g., a speaker or headphones).

In some embodiments, media output component 215 may be configured to present a graphical user interface (e.g., a web browser and/or a client application) to user 201. A graphical user interface may include, for example, an online store interface for viewing and/or purchasing items, and/or a wallet application for managing payment information. In some embodiments, client device 202 may include an input device 220 for receiving input from user 201. User 201 may use input device 220 to, without limitation, select and/or enter data, such as, for example, one or more report criteria or report filters.

Input device 220 may include, for example, a keyboard, a pointing device, a mouse, a stylus, a touch sensitive panel (e.g., a touch pad or a touch screen), a gyroscope, an accelerometer, a position detector, a biometric input device, and/or an audio input device. A single component such as a touch screen may function as both an output device of media output component 215 and input device 220.

Client device 202 may also include a communication interface 225, communicatively coupled via network 110 to web server 112 (shown in FIG. 1). Communication interface 225 may include, for example, a wired or wireless network adapter and/or a wireless data transceiver for use with a mobile telecommunications network.

Stored in memory area 210 are, for example, computer readable instructions for providing a user interface to user 201 via media output component 215 and, optionally, receiving and processing input from input device 220. A user interface may include, among other possibilities, a web browser and/or a client application. Web browsers enable users, such as user 201, to display and interact with media and other information typically embedded on a web page or a website.

Exemplary Database System

Figure 3:
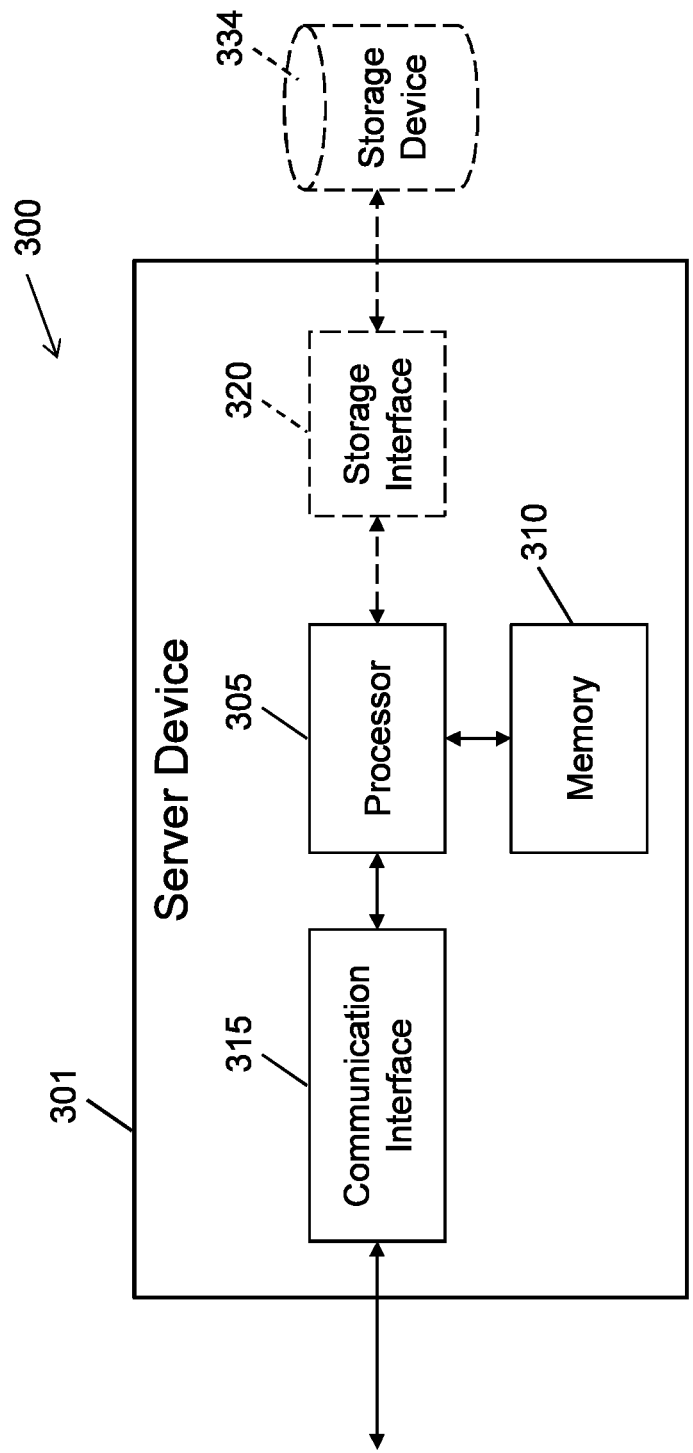
FIG. 3 illustrates an exemplary configuration of a server shown in FIG. 1, in accordance with one embodiment of the present disclosure.

FIG. 3 depicts an exemplary database system 300 such as database server 114 and database 116, as shown in FIG. 1, and in accordance with one exemplary embodiment of the present disclosure. Accordingly, database system 300 may include a server computer device 301 (e.g., database server 114), which may, in turn, include a processor 305 for executing instructions. Instructions may be stored in a memory area 310. Processor 305 may include one or more processing units (e.g., in a multi-core configuration).

Processor 305 may be operatively coupled to a communication interface 315 such that server computer device 301 is capable of communicating with a remote computing device, as described above. For example, communication interface 315 may receive requests from client device 202 via the Internet and/or over a computer network.

Processor 305 may also be operatively coupled to a storage device 334 (e.g., database 116). Storage device 334 may be any computer-operated hardware suitable for storing and/or retrieving data, such as, but not limited to, data associated with database 320. In some embodiments, storage device 334 may be integrated in server computer device 301. For example, server computer device 301 may include one or more hard disk drives as storage device 334.

In other embodiments, storage device 334 may be external to server computer device 301 and may be accessed by a plurality of server computer devices 301. For example, storage device 334 may include a storage area network (SAN), a network attached storage (NAS) system, and/or multiple storage units such as hard disks and/or solid state disks in a redundant array of inexpensive disks (RAID) configuration.

In some embodiments, processor 305 may be operatively coupled to storage device 334 via a storage interface 320. Storage interface 320 may be any component capable of providing processor 305 with access to storage device 334. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 334.

Exemplary Data Table

FIG. 4 illustrates a data table 400 for use with system 100. More particularly, data table 400 illustrates one format in which data may be stored by database 116. Specifically, data may be stored as part of a "flexible schema," in which data values are not stored in association with a particular field but rather as data strings, such as data strings 402, 404, and 406. Each string 402-406 may include a plurality of data values, which may be separated by commas, and which may be associated with a particular user id (or UID), such as UIDs 408, 410, and 412, respectively. Strings 402-406 of data values may be organized by database server 114 and/or web server 112 when strings 402-406 are read out of database 116. For example, web server 112 may read data values from each string 402-406 when strings 402-406 are accessed, such that web server 112 may determine that a first user (associated with UID 408) had a heart rate ("hr") of 75 beats per minute and logged a total of 8,000 steps on a particular day.

Exemplary Message Broker

Figure 5:
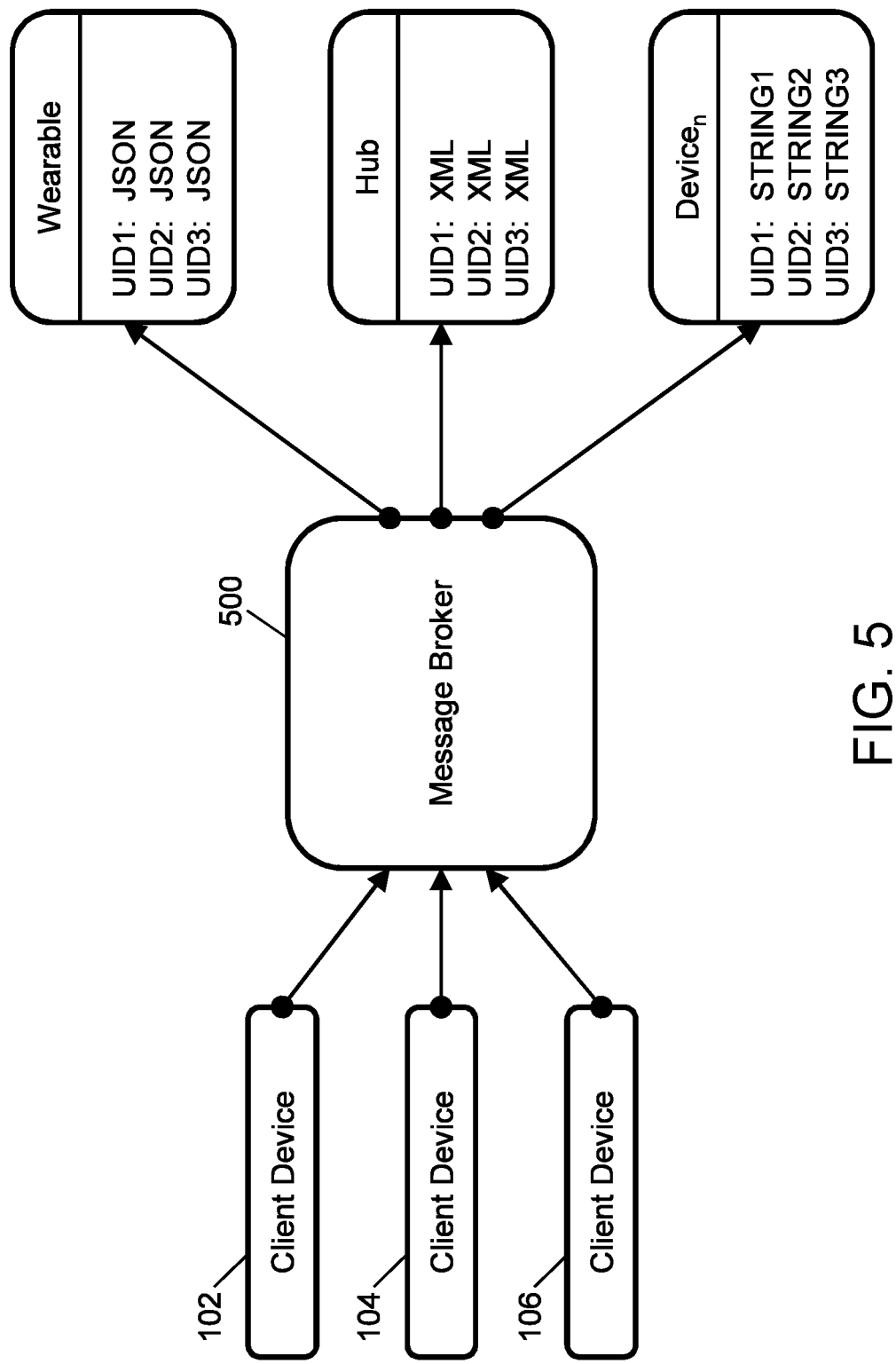
FIG. 5 illustrates a schematic diagram of an exemplary message broker that may execute on the system shown in FIG. 1.

FIG. 5 illustrates a schematic diagram of an exemplary message broker 500 that may execute on system 100, such as, for example, on web server 112. As described above, message broker 500 may be configured to translate messages or communications from a messaging protocol of a sending device to a messaging protocol of a receiving device. For instance, as shown message broker 500 may translate messages received from client devices 102-108 from protocols associated with each client device 102-108 to one or more other protocols or message formats for storage in database 116, such as, for example, a JSON format, an XML format, a string or flexible schema format (as described above), and the like.

Exemplary Process for Generating a Health Score

FIG. 6 depicts a flow chart of an exemplary computer-implemented process 600 for risk assessment. Accordingly, in the exemplary embodiment, web server 112 (or a processor thereof) may receive, from a client device 102-108, data associated with a user, such as various lifestyle data. For instance, in some embodiments, web server 112 may receive lifestyle data including one or more of biometric data, health data, vehicle data, and/or personal data associated with a user (step 602). Various examples of biometric data, home data, vehicle data, and/or personal data are described above.

Having received such data, web server 112 may, in addition, analyze the biometric data, home data, vehicle data, and/or personal data (step 604). For instance, web server 112 may analyze the various data to determine a health score associated with the user (step 606). The analysis may be based upon a plurality of rules, such as, for example, a plurality of rules for determining a health score of the user based upon the various lifestyle data. For instance, biometric data indicating that the user's weight has decreased may improve the user's health score, while biometric data indicating that the user's weight has increased may diminish the user's health score.

The health score may, in addition, represent a likelihood that the user will maintain a level of health for a predefined period of time, such as a period of time corresponding to a term of an insurance policy. Thus, the health score may be associated with or correspond to a mortality risk, such as, for example, a risk of death. The health score may, in addition, be based upon the data, such that the health score improves with improvements to the user's health and/or such that the health score diminishes with reductions in the user's health. In other words, the health score may increase in response to lifestyle data suggesting that the user is healthy, or that the user's health may be improving, and the health score may decrease in response to lifestyle data suggesting that the user is unhealthy, or that the user's health may be negatively affected by one or more lifestyle activities, such as cigarette smoking or weight gain. Such determinations may be made based upon the plurality of rules.

The health score may also increase and decrease based upon vehicle data, home data, and/or personal data. For instance, the health score associated with the user may decrease as a result of unsafe driving operations or behaviors performed by the user (e.g., high g maneuvers as detected by an accelerometer of the user's vehicle) and/or as a result of driving in high crime or high traffic incident areas or regions (e.g., as determined based upon GPS data). Similarly, the health score of the user may decrease as a result of home data indicating that the user regularly consumes unhealthy foods and/or beverages, and/or home data indicating that an air quality within the user's home is insufficiently unhealthy.

The health score of the user may increase, on the other hand, as a result of home data indicating that the user eats healthy foods and/or that the air quality within the user's home is clean or otherwise sufficiently healthy. In addition, the health score of the user may decrease based upon personal data, such as social networking data indicating that the user regularly engages in unsafe or hazardous behaviors or activities, and the like. On the other hand, the health score of the user may increase based upon personal data indicating that the user does not engage is unsafe or hazardous activities and/or, for example, that the user has children and is predisposed to lifestyle choices that may suggest a longer lifespan.

Having determined a health score for the user, web server 112 may, in addition, retrieve one or more terms and conditions for an insurance policy from a database (e.g., database 116) (step 608). The terms and conditions may include any terms and conditions necessary or appropriate to an insurance policy, such as a life insurance policy, applied for by the user. For example, the terms and conditions may include a term for the policy (e.g., in years), a premium for the policy (e.g., in dollars), and the like. The dollar amount of the premium may be proportional to the health score. For instance, a low health score may result in a low or reduced, premium, and a low health score may result in a higher or increased premium. Web server 112 may also generate a life insurance policy for the user based, at least in part, upon the retrieved terms and conditions (step 610).

Thus, system 100 may collect a variety of lifestyle data for a particular user, such as biometric data obtained from a wearable electronic device, home data obtained from electronic devices within a home or dwelling of the user, vehicle data obtained from electronic devices within a vehicle of the user, and/or personal data, such as social networking data, obtained from a smartphone or other client device of the user. System 100 may, in addition, analyze the data collected for the user to determine a health score of the user, and, in response, system 100 may generate a life insurance policy, including an introductory or initial life insurance premium for the user.

In various embodiments, other types of insurance policies (e.g., auto insurance policies, property and casualty insurance policies, medical insurance policies, and the like) may be generated based upon the data collected and in like manner. For example, an auto insurance policy may be generated based upon vehicle data, such as driving history or driving behavior. Similarly, a medical insurance policy may be generated based upon biometric and/or personal data.

Exemplary Process for Updating a Health Score

FIG. 7 depicts a flow chart of an exemplary computer-implemented process 700 for updating a health score associated with a user. Accordingly, in the exemplary embodiment, web server 112 (or a processor thereof) may generate an initial health score for a user (as described above). For example, web server 112 may receive, from a client device 102-108, lifestyle data associated with a user to generate an initial health score for the user. This lifestyle data may include biometric data, health data, vehicle data, and/or personal data associated with a user.

To generate an updated health score, web server 112 may, as described above (with reference to FIG. 6), generate a life insurance policy based upon an initial set of lifestyle data, such as biometric data, health data, vehicle data, and/or personal data (step 702). Web server 112 may also receive updated lifestyle data, such as, for example, updated biometric data, health data, vehicle data, and/or personal data associated (step 704). Various examples of biometric data, home data, vehicle data, and/or personal data are described above. The updated lifestyle data may, in addition, be obtained later in time or as follow up data to data used to generate an initial insurance policy or insurance premium.

Having received the updated lifestyle data, web server 112 may, in addition, analyze the updated biometric data, home data, vehicle data, and/or personal data (step 706). For instance, web server 112 may analyze the various updated data (e.g., based upon a plurality of rules, as described above) to determine an updated health score associated with the user (steps 706 and 708). Here, as above, the updated health score may be associated with a mortality risk, which may be indicative of a risk of death associated with the user. The health score may, in addition, be updated based upon the data, such that the health score improves with improvements to the user's health and/or such that the health score diminishes with reductions in the user's health. In other words, the updated health score may increase in response to updated lifestyle data suggesting that the user is healthy, or that the user's health may be improving, and the health score may decrease in response to updated lifestyle data suggesting that the user is unhealthy, or that the user's health may be negatively affected by one or more lifestyle activities, such as cigarette smoking or weight gain.

The health score may also be updated to increase and decrease based upon vehicle data, home data, and/or personal data. For instance, the health score associated with the user may be updated to decrease as a result of unsafe driving operations or behaviors performed by the user (e.g., high g maneuvers as detected by an accelerometer of the user's vehicle) and/or as a result of driving in high crime and/or high traffic incident areas or regions (e.g., as determined based upon GPS data). Similarly, the health score of the user may be updated to decrease as a result of home data indicating that the user regularly consumes unhealthy foods and/or beverages, and/or home data indicating that an air quality within the user's home is insufficiently healthy. The health score of the user may be updated to increased, on the other hand, as a result of home data indicating that the user eats healthy foods and/or that the air quality within the user's home is clean or otherwise sufficiently healthy. In addition, the health score of the user may be updated to decrease based upon personal data, such as social networking data indicating that the user regularly engages in unsafe or hazardous behaviors or activities, and the like. On the other hand, the health score of the user may be updated to increase based upon personal data indicating that the user does not engage is unsafe or hazardous activities and/or, for example, that the user has children and is predisposed to lifestyle choices that may suggest a longer lifespan.

Having determined an updated health score for the user, web server 112 may, in addition, retrieve updated terms and conditions for an insurance policy from a database (e.g., database 116) (step 710). As described above, the updated terms and conditions may include any terms and conditions necessary or appropriate to an insurance policy, such as a life insurance policy, applied for by the user. For example, the updated terms and conditions may include an updated term for the policy (e.g., in years), an updated premium for the policy (e.g., in dollars), and the like. The dollar amount of the premium may be proportional to the updated health score. For instance, a low health score may result in a low or reduced, updated premium, and a low health score may result in a higher or increased updated premium. Web server 112 may also generate an updated life insurance policy for the user based, at least in part, upon the retrieved updated terms and conditions (step 712).

Thus, system 100 may collect a variety of data for a particular user, such as biometric data obtained from a wearable electronic device, home data obtained from electronic devices within a home or dwelling of the user, vehicle data obtained from electronic devices within a vehicle of the user, and/or personal data, such as social networking data, obtained from a smartphone or other client device of the user. System 100 may, in addition, analyze the data collected for the user to update a previously determined health score of the user, and, in response, system 100 may generate an updated life insurance policy and/or an updated life insurance premium for the user.

In various embodiments, other types of insurance policies (e.g., auto insurance policies, property and casualty insurance policies, medical insurance policies, and the like) may be updated based upon the data collected and in like manner. For example, an auto insurance policy may be updated based upon vehicle data, such as driving history or driving behavior. Similarly, a medical insurance policy may be updated based upon biometric and/or personal data.

Exemplary Embodiments & Functionality

In one aspect, a computer system for analyzing biometric data of a user collected from a plurality of user devices and used to generate an insurance policy for the user is provided. In some exemplary embodiments, the computer system includes a processor and a non-transitory, tangible, computer-readable storage medium having instructions stored thereon that, in response to execution by the processor, cause the processor to perform operations including: (i) receiving, from a wearable electronic user device, biometric data associated with a user; (ii) analyzing, based upon a plurality of rules, the biometric data; (iii) determining a health score associated with the user, based in part upon the analysis of the biometric data, wherein the health score represents a likelihood that the user will maintain a level of health for a predefined period of time; (iv) retrieving terms and conditions for an insurance policy from a database based upon the health score; and (v) generating, based upon the determining, an insurance policy for the user based upon the terms and conditions.

In another aspect, at least one tangible, non-transitory, computer readable storage media having computer-executable instructions embodied thereon, wherein when executed by at least one processor, the computer-executable instructions cause the processor to: (i) receive, from a wearable electronic user device, biometric data associated with a user; (ii) analyze, based upon a plurality of rules, the biometric data; (iii) determine a health score associated with the user, based in part upon the analysis of the biometric data, wherein the health score represents a likelihood that the user will maintain a level of health for a predefined period of time; (iv) retrieve terms and conditions for an insurance policy from a database based upon the health score; and (v) generate, based upon the determining, an insurance policy for the user based upon the terms and conditions.

In yet another aspect, a method computer system for analyzing biometric data of a user collected from a plurality of user devices and used to generate an insurance policy for the user is provided. The method includes (i) receiving, from a wearable electronic user device, biometric data associated with a user; (ii) analyzing, based upon a plurality of rules, the biometric data; (iii) determining a health score associated with the user, based in part upon the analysis of the biometric data, wherein the health score represents a likelihood that the user will maintain a level of health for a predefined period of time; (iv) retrieving terms and conditions for an insurance policy from a database based upon the health score; and (v) generating, based upon the determining, an insurance policy for the user based upon the terms and conditions.

In yet another aspect, a computer system for analyzing biometric data of a user collected from a plurality of user devices and used to generate an insurance policy for the user is provided. In some exemplary embodiments, the computer system includes a processor and a non-transitory, tangible, computer-readable storage medium having instructions stored thereon that, in response to execution by the processor, cause the processor to perform operations including: (i) generating a life insurance policy for a user based upon an initial set of biometric data; (ii) receiving, from the wearable electronic device, updated biometric data associated with the user; (iii) analyzing, based upon a plurality of rules, the updated biometric data; (iv) determining, based in part upon the analysis of the updated biometric data, an updated health score associated with the user, wherein the updated health score represents an updated likelihood that the user will maintain a level of health for a predefined period of time; (v) retrieving, based upon the determining, updated terms and conditions for an insurance policy from a database based upon the updated health score; and (vi) updating, based upon the determining, the life insurance policy for the user.

Machine Learning & Other Matters

The computer-implemented methods discussed herein may include additional, less, or alternate actions, including those discussed elsewhere herein. The methods may be implemented via one or more local or remote processors, transceivers, servers, and/or sensors (such as processors, transceivers, servers, and/or sensors mounted on vehicles or mobile devices, or associated with smart infrastructure or remote servers), and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as image, mobile device, vehicle telematics, autonomous vehicle, and/or intelligent home telematics data. The machine learning programs may utilize deep learning algorithms that may be primarily focused on pattern recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or machine learning.

In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs.

Additional Considerations

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A computer system for determining a health score and generating an insurance policy for a user, the computer system comprising:
   a processor; and
   a non-transitory, tangible, computer-readable storage medium having instructions stored thereon that, in response to execution by the processor, cause the processor to perform operations comprising:
      receiving first user data from a smart infrastructure comprising at least one smart device, wherein the first user data includes first lifestyle data associated with a user over a first time period;
      receiving second user data from the smart infrastructure, wherein the second user data includes second lifestyle data associated with the user over a second time period;
      analyzing the first user data and the second user data to assess a current level of health of the user;

determining a health score based at least in part upon the analysis of the first user data and the second user data, wherein the health score represents a likelihood that the user will maintain the current level of health for a period of time corresponding to a term of a life insurance policy;

selecting, based upon the health score, a set of terms and conditions from a plurality of sets of terms and conditions stored in a database, wherein the set of terms and conditions includes the period of time corresponding to the term; and generating, based upon the health score and the set of terms and conditions, an insurance policy associated with the current level of health of the user, wherein the insurance policy is based upon the period of time during which the health score represents the likelihood that the user will maintain the current level of health.

2. The computer system of claim 1, wherein the processor is further configured to perform operations comprising:

receiving, from a wearable electronic device, biometric data associated with the user;

analyzing the first user data and the second user data associated with the user, at least one of the first user data or the second user data including the biometric data, to assess the current level of health of the user;

determining the health score based at least in part upon the analysis of the biometric data; and generating, based upon the health score, the insurance policy.

3. The computer system of claim 2, wherein the biometric data includes at least one of skin temperature data, heart rate data, body mass index data, resting heart rate data, exercise intensity data, calories burned data, sleep duration data, REM sleep duration data, electrocardiogram data, VO2 max data, steps data, floors climbed data, blood pressure data, blood oxygen content data, weight data, and height data.

4. The computer system of claim 1, wherein the processor is further configured to perform operations comprising:

receiving, from a home based device, home data associated with the user wherein the home data includes at least one of environmental air quality data, home temperature data, ultraviolet radiation exposure data, carbon dioxide data, and carbon monoxide data;

analyzing the first user data and the second user data associated with the user, at least one of the first user data or the second user data including the home data, to assess the current level of health of the user; and determining the health score based at least in part upon the analysis of the home data.

5. The computer system of claim 1, wherein the processor is further configured to perform operations comprising:

receiving, from a vehicle based device, vehicle data associated with the user, wherein the vehicle data includes at least one of vehicle safety rating data and driving behavior data;

analyzing the first user data and the second user data associated with the user, at least one of the first user data or the second user data including the vehicle data, to assess the current level of health of the user; and determining the health score based at least in part upon the analysis of the vehicle data.

6. The computer system of claim 1, wherein the processor is further configured to perform operations comprising:

receiving personal data associated with the user;

analyzing the first user data and the second user data associated with the user, at least one of the first user data or the second user data including the personal data, to assess the current level of health of the user; and determining the health score based at least in part upon the analysis of the personal data.

7. The computer system of claim 1, wherein the processor is further configured to perform operations comprising:

analyzing the first user data and the second user data associated with the user to assess the current level of health of the user by applying a plurality of rules;

determining the health score, wherein the health score represents improvements or deteriorations to an overall health of the user based upon the analysis; and retrieving, based upon the health score, terms and conditions for the insurance policy from a database, wherein the terms and conditions stored in the database are linked to a respective health score, and wherein the retrieved terms and conditions include the term of the insurance policy and an insurance premium proportional to the determined health score.

8. At least one tangible, non-transitory, computer-readable storage media having computer-executable instructions embodied thereon, wherein when executed by at least one processor, the computer-executable instructions cause the processor to:

receive first user data from a smart infrastructure comprising at least one smart device, wherein the first user data includes first lifestyle data associated with a user over a first time period;

receive second user data from the smart infrastructure, wherein the second user data includes second lifestyle data associated with the user over a second time period;

analyze the first user data and the second user data to assess a current level of health of the user;

determine a health score based at least in part upon the analysis of the first user data and the second user data, wherein the health score represents a likelihood that the user will maintain the current level of health for a period of time corresponding to a term of a life insurance policy;

select, based upon the health score, a set of terms and conditions from a plurality of sets of terms and conditions stored in a database, wherein the set of terms and conditions includes the period of time corresponding to the term; and generate, based upon the health score and the set of terms and conditions, an insurance policy associated with the current level of health of the user, wherein the insurance policy is based upon the period of time during which the health score represents the likelihood that the user will maintain the current level of health.

9. The computer-readable storage media of claim 8, wherein the computer-executable instructions further cause the processor to:

receive, from a wearable electronic device, biometric data associated with the user;

analyze the first user data and the second user data associated with the user, at least one of the first user data or the second user data including the biometric data, to assess the current level of health of the user;

determine the health score based at least in part upon the analysis of the biometric data; and generate, based upon the health score, the insurance policy.

10. The computer-readable storage media of claim 9, wherein the biometric data includes at least one of skin temperature data, heart rate data, body mass index data, resting heart rate data, exercise intensity data, calories burned data, sleep duration data, REM sleep duration data, electrocardiogram data, VO2 max data, steps data, floors climbed data, blood pressure data, blood oxygen content data, weight data, and height data.

11. The computer-readable storage media of claim 8, wherein the computer-executable instructions further cause the processor to:
receive, from a home based device, home data associated with the user wherein the home data includes at least one of environmental air quality data, home temperature data, ultraviolet radiation exposure data, carbon dioxide data, and carbon monoxide data;
analyze the first user data and the second user data associated with the user, at least one of the first user data or the second user data including the home data, to assess the current level of health of the user; and
determine the health score based at least in part upon the analysis of the home data.

12. The computer-readable storage media of claim 8, wherein the computer-executable instructions further cause the processor to:
receive, from a vehicle based device, vehicle data associated with the user, wherein the vehicle data includes at least one of vehicle safety rating data and driving behavior data;
analyze the first user data and the second user data associated with the user, at least one of the first user data or the second user data including the vehicle data, to assess the current level of health of the user; and
determine the health score based at least in part upon the analysis of the vehicle data.

13. The computer-readable storage media of claim 8, wherein the computer-executable instructions further cause the processor to:
receive personal data associated with the user;
analyze the first user data and the second user data associated with the user, at least one of the first user data or the second user data including the personal data, to assess the current level of health of the user; and
determine the health score based at least in part upon the analysis of the personal data; and
retrieve, based upon the health score, terms and conditions for the insurance policy from a database, wherein the terms and conditions stored in the database are linked to a respective health score, and wherein the retrieved terms and conditions include the term of the insurance policy and an insurance premium proportional to the determined health score.

14. The computer-readable storage media of claim 8, wherein the computer-executable instructions further cause the processor to:
analyze the first user data and the second user data associated with the user to assess the current level of health of the user by applying a plurality of rules; and
determine the health score, wherein the health score represents improvements or deteriorations to an overall health of the user based upon the analysis.

15. A method for determining a health score and generating an insurance policy for a user comprising:
receiving first user data from a smart infrastructure comprising at least one smart device, wherein the first user data includes first lifestyle data associated with a user over a first time period;
receiving second user data from the smart infrastructure, wherein the second user data includes second lifestyle data associated with the user over a second time period;
analyzing the first user data and the second user data to assess a current level of health of the user;
determining a health score based at least in part upon the analysis of the first user data and the second user data, wherein the health score represents a likelihood that the user will maintain the current level of health for a period of time corresponding to a term of a life insurance policy;
selecting, based upon the health score, a set of terms and conditions from a plurality of sets of terms and conditions stored in a database, wherein the set of terms and conditions includes the period of time corresponding to the term; and
generating, based upon the health score and the set of terms and conditions, an insurance policy associated with the current level of health of the user, wherein the insurance policy is based upon the period of time during which the health score represents the likelihood that the user will maintain the current level of health.

16. The method of claim 15, further comprising:
receiving, from a wearable electronic device, biometric data associated with the user;
analyzing the first user data and the second user data associated with the user, at least one of the first user data or the second user data including the biometric data, to assess the current level of health of the user;
determining the health score based at least in part upon the analysis of the biometric data; and
generating, based upon the health score, the insurance policy.

17. The method of claim 16, wherein the biometric data includes at least one of skin temperature data, heart rate data, body mass index data, resting heart rate data, exercise intensity data, calories burned data, sleep duration data, REM sleep duration data, electrocardiogram data, VO2 max data, steps data, floors climbed data, blood pressure data, blood oxygen content data, weight data, and height data.

18. The method of claim 15, further comprising:
receiving, from a home based device, home data associated with the user wherein the home data includes at least one of environmental air quality data, home temperature data, ultraviolet radiation exposure data, carbon dioxide data, and carbon monoxide data;
analyzing the first user data and the second user data associated with the user, at least one of the first user data or the second user data including the home data, to assess the current level of health of the user; and
determining the health score based at least in part upon the analysis of the home data.

19. The method of claim 15, further comprising:
receiving, from a vehicle based device, vehicle data associated with the user, wherein the vehicle data includes at least one of vehicle safety rating data and driving behavior data;
analyzing the first user data and the second user data associated with the user, at least one of the first user data or the second user data including the vehicle data, to assess the current level of health of the user; and
determining the health score based at least in part upon the analysis of the vehicle data.

20. The method of claim 15, further comprising:
receiving personal data associated with the user;
analyzing the first user data and the second user data associated with the user, at least one of the first user data or the second user data including the personal data, to assess the current level of health of the user; and determining the health score based at least in part upon the analysis of the personal data.

21. A computer system for analyzing biometric data of a user collected from a plurality of user devices and used to generate an insurance policy for the user, the computer system comprising:

a processor; and a non-transitory, tangible, computer-readable storage medium having instructions stored thereon that, in response to execution by the processor, cause the processor to perform operations comprising:

generating a life insurance policy for a user based upon an initial set of user data from a smart infrastructure comprising at least one smart device, wherein the user data includes lifestyle data associated with the user over a first time period;

receiving updated user data from the smart infrastructure, wherein the updated user data includes second lifestyle data associated with the user over a second time period;

analyzing the updated user data to assess an updated level of health of the user;

determining an updated health score associated with the user, wherein the updated health score represents an updated likelihood that the user will maintain the updated level of health for a period of time corresponding to a term of a life insurance policy;

selecting, based upon the updated health score, a set of terms and conditions from a plurality of sets of terms and conditions stored in a database, wherein the set of terms and conditions includes the period of time corresponding to the term; and updating, based upon the updated health score and the set of terms and conditions, the life insurance policy associated with the updated level of health of the user, wherein the insurance policy is based upon the period of time during which the health score represents the likelihood that the user will maintain the updated level of health.

* * * * *